(12) United States Patent
Trice

(10) Patent No.: US 6,371,959 B1
(45) Date of Patent: Apr. 16, 2002

(54) RADIOLUCENT POSITION LOCATING DEVICE AND DRILL GUIDE

(76) Inventor: Michael E. Trice, 2240 W. Packard Ave., Decatur, IL (US) 62522

(*) Notice: Subject to any disclaimer, the term of this patent is extended or adjusted under 35 U.S.C. 154(b) by 0 days.

(21) Appl. No.: 09/543,659

(22) Filed: Apr. 5, 2000

(51) Int. Cl.$^7$ .............................................. A61B 17/56
(52) U.S. Cl. ........................................................ 606/97
(58) Field of Search .............................. 606/96, 97, 98, 606/80, 87, 62, 64

(56) References Cited

U.S. PATENT DOCUMENTS

| | | | |
|---|---|---|---|
| 2,622,592 A | | 12/1952 | Rosenstein |
| 4,621,628 A | * | 11/1986 | Brudermann ................. 606/64 |
| 4,803,976 A | * | 2/1989 | Frigg et al. .................... 33/286 |
| 4,850,344 A | | 7/1989 | Olerud et al. |
| 4,917,111 A | | 4/1990 | Pennig et al. |
| 4,969,889 A | * | 11/1990 | Greig ........................... 606/96 |
| 4,978,351 A | * | 12/1990 | Rozas ........................... 606/96 |
| 5,403,321 A | | 4/1995 | DiMarco |
| 6,074,394 A | * | 6/2000 | Krause ......................... 606/86 |

FOREIGN PATENT DOCUMENTS

WO      WO91/03982      4/1991

* cited by examiner

*Primary Examiner*—Eduardo C. Robert
(74) *Attorney, Agent, or Firm*—The Maxham Firm

(57) ABSTRACT

A method and apparatus for establishing and maintaining coaxial alignment with a transverse hole in an osteosynthesis aid in a bone. The method comprises placing a guide sleeve next to the bone, where one end of the sleeve is shaped to indent the bone. Then a radiolucent plug is inserted into the guide sleeve, the plug having a radiographic pin centrally located along the plug's long axis. The pin is then coaxially aligned with the transverse hole in the osteosynthesis aid and the pin and guide sleeve are driven into the bone, to prevent relative movement between the bone and the sleeve. The radiolucent plug is removed and a drill is placed into the guide sleeve for drilling a hole into the bone. The drill is then removed, a fastener is placed into the guide sleeve and driven into the bone and into the transverse hole in the osteosynthesis aid.

12 Claims, 7 Drawing Sheets

RADIOLUCENT POSITION LOCATING DEVICE AND DRILL GUIDE

BACKGROUND OF THE INVENTION

1. Field of the Invention

The present invention generally relates to aiming, guiding, and hole forming for surgical procedures, and more particularly to a method and apparatus for determining coaxial alignment between fasteners and holes in a device which has been located within a bone.

2. Discussion of the Related Art

It is well known that many damaged and broken bones are repaired by the insertion by an intramedullary rod or pin. Also known as osteosynthesis aids, these rods or pins facilitate connection of the bone pieces together and are usually placed in the long axis of the damaged bone. If the bone is broken into two or more parts the rod stabilizes and secures the bone parts relative to each other to aid in proper healing and it also supports the bone during the healing process. Such a rod can have one, or more, holes drilled perpendicular to its longitudinal axis to allow fasteners to be inserted through the bone and into the rod to fix the rod's location in the bone. In many instances holes must be drilled, or otherwise formed, in the bone before fasteners can be inserted through the bone and into the transverse rod holes. Of course, it is not possible to see the hole, or holes, in the rod once the rod has been inserted within the bone, so X-ray means are used to view the rod through the bone and determine where the transverse holes are located in the intramedullary rod.

Once the transverse intramedullary rod holes are found and their orientation is determined, a matching hole or set of holes must be formed in the bone. It is vital that holes formed in the bone and their matching rod holes are coaxially aligned. This coaxial alignment results in fasteners that are concentrically aligned with the rod holes, which assures that the fasteners indeed engage the rod holes and that the bone parts are not twisted or misaligned relative to each other when the fastener is inserted in the rod.

Aiming devices for coaxial bone hole formation are known in the art. They include spaced rings and wires which help the doctor determine the correct coaxial alignment for the hole, or holes, to be drilled in the bone. A source of X-ray radiation is arranged on one side of the procedure area, with an X-ray receiver on the other side. The doctor views the fractured bone, intramedullary rod, and aiming device through a X-ray imaging screen. The doctor then uses such an aiming device to determine the correct location and orientation for the holes to be drilled in the bone.

One of the problems encountered during the procedure is that once the correct orientation and location of the hole to be drilled in the bone has been found, the alignment device may drift on the slick bone surface or otherwise lose the correct orientation from contact with surrounding soft tissue and therefore the resulting hole is no longer optimally aligned. Additionally, if a drill is used to drill a hole through the bone, the drill can slip from the desired location and the resulting hole will be misaligned. Moreover, the drill must be maintained at the desired orientation throughout the drilling procedure, or else the resulting hole will not be coaxially aligned with the rod hole.

SUMMARY OF THE INVENTION

The present invention solves the problem of undesirable movement during a procedure with a cannulated system that allows for quick and accurate coaxial alignment with transverse holes located in a rod. Also, the invention allows for accurate location of a drill, accurate guiding of the drill, and also accurate guidance for fasteners, which are inserted through the bone and into the transverse holes.

Broadly, the present invention concerns a method and apparatus for determining and maintaining coaxial alignment with transverse intramedullary rod holes. More specifically, one embodiment of the invention uses a radiographic pin centrally mounted in a cylindrical it radiolucent plug, the plug being slidably engaged in a cannula, or guide sleeve, having a sharp edge which is placed against a bone. Using X-ray means, the pin is used to coaxially align the cannula with the transverse intramedullary rod hole, and then the sharp edge of the cannula is driven into the bone sufficiently to make an impression, establishing a guide sleeve position that is properly oriented throughout a medical procedure. The pin is also driven into the bone, creating an indentation that acts as a pilot-hole, or marking point, for a drill which is inserted in the guide sleeve after the pin and plug assembly is removed. The drill uses the sleeve as a guide to ensure proper coaxial alignment with the rod hole. Once a hole is drilled the drill is removed from the guide sleeve and a fastener is inserted in the sleeve. Again, the sleeve is used as a guide to ensure proper alignment of the fastener into the bone and into the transverse hole in the rod.

The invention affords its users with a number of distinct advantages. Unlike prior alignment systems, the present invention uses a cannulated system to secure a guide sleeve firmly against the bone which allows for an alignment, once determined, to remain accurate throughout the procedure. Also, a guide pin is used to create an indentation, or mark, in the bone which acts as a starting point and guide for the drilling operation. Additionally, the sleeve system guides the drill for its drilling operation, and also guides the fastener. Thus, the aiming and guiding apparatus according to the invention not only quickly and accurately determines proper coaxial alignment, but it assures correct alignment throughout the medical procedure.

BRIEF DESCRIPTION OF THE DRAWING

The nature, objects, and advantages of the invention will become more apparent to those skilled in the art after considering the following detailed description in connection with the It accompanying drawing, in which like reference numerals designate like parts throughout, wherein.

DETAILED DESCRIPTION OF THE PREFERRED EMBODIMENTS

General

Throughout this description, the preferred embodiment and examples shown should be considered as exemplars, rather than as limitations on the present invention.

Broadly, the present invention comprises a method and apparatus for determining coaxial alignment with transverse holes in intramedullary rods or pins. The invention is especially effective when used to align, drill holes for, and guide, cross-screws into transverse holes in an osteosynthesis aid located in a fractured bone.

The alignment apparatus of this invention includes a bone-engaging guide sleeve that uses a radiolucent plug with an encased radiographic wire so that once proper alignment is determined with the wire, the guide sleeve acts as a guide or centering mechanism during the drilling and fastener insertion procedures. This provides a secure centering mechanism that prevents the possibility of soft tissue pushing the drill out of position, which generally results in misalignment.

The present invention has a guide sleeve employing a radiographic wire fixably mounted in a radiolucent plug that is removable from the guide sleeve. The plug with the wire inserted therein insures that the sleeve is aligned with the rod hole, and it allows use of a larger diameter sleeve that is more stable on the bone surface. The guide sleeve is affixed to the bone and it has a wide stance which results in a stable position on the slick bone. Thus, holes are drilled accurately, as the patient's soft tissue is prevented from pushing the sleeve out of alignment.

Figure 1:
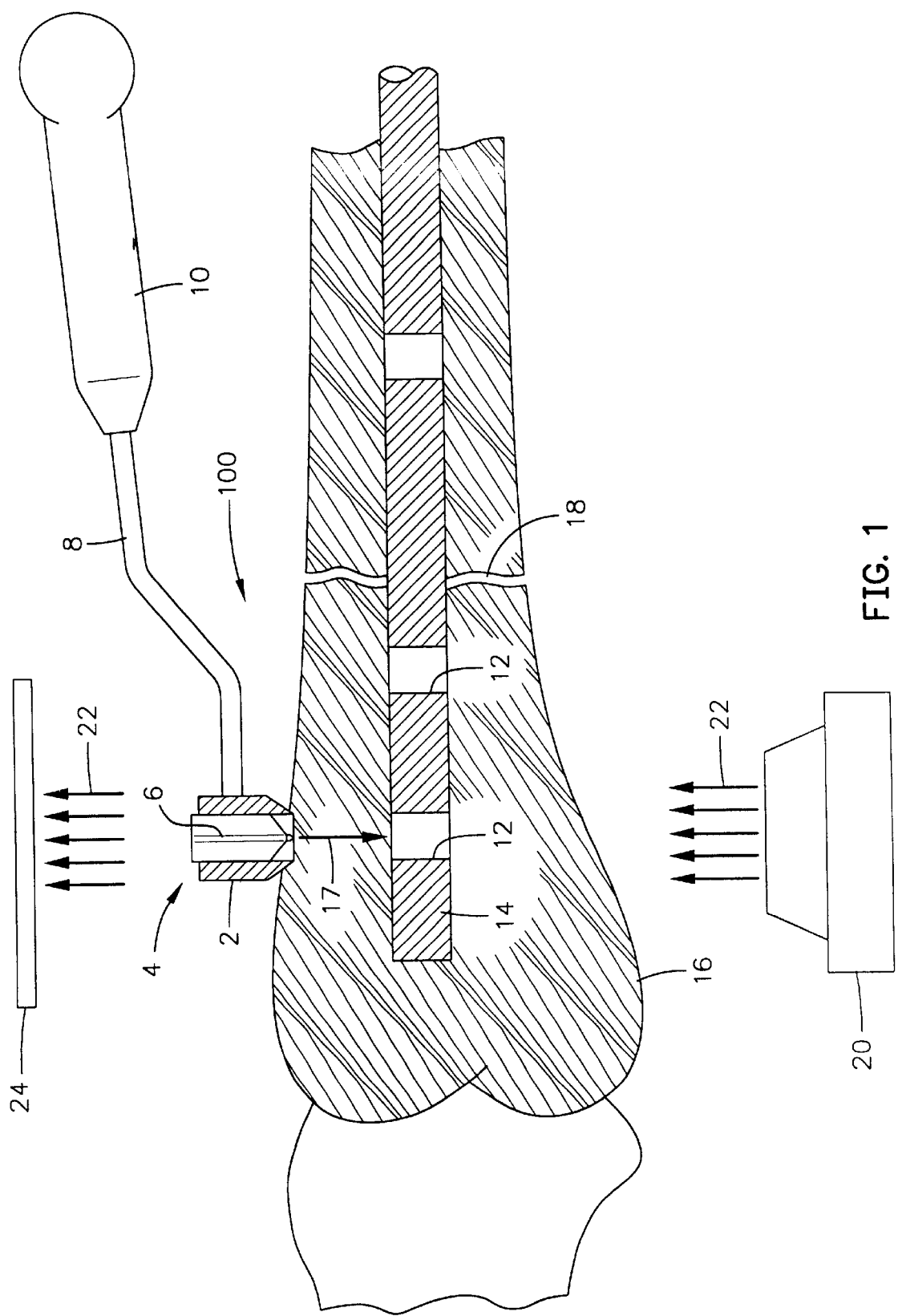
FIG. 1 is a partial sectional side view showing the relationship between a fractured bone having an osteosynthesis aid therein, X-ray means, and a preferred embodiment of the present invention.
Figure 2:
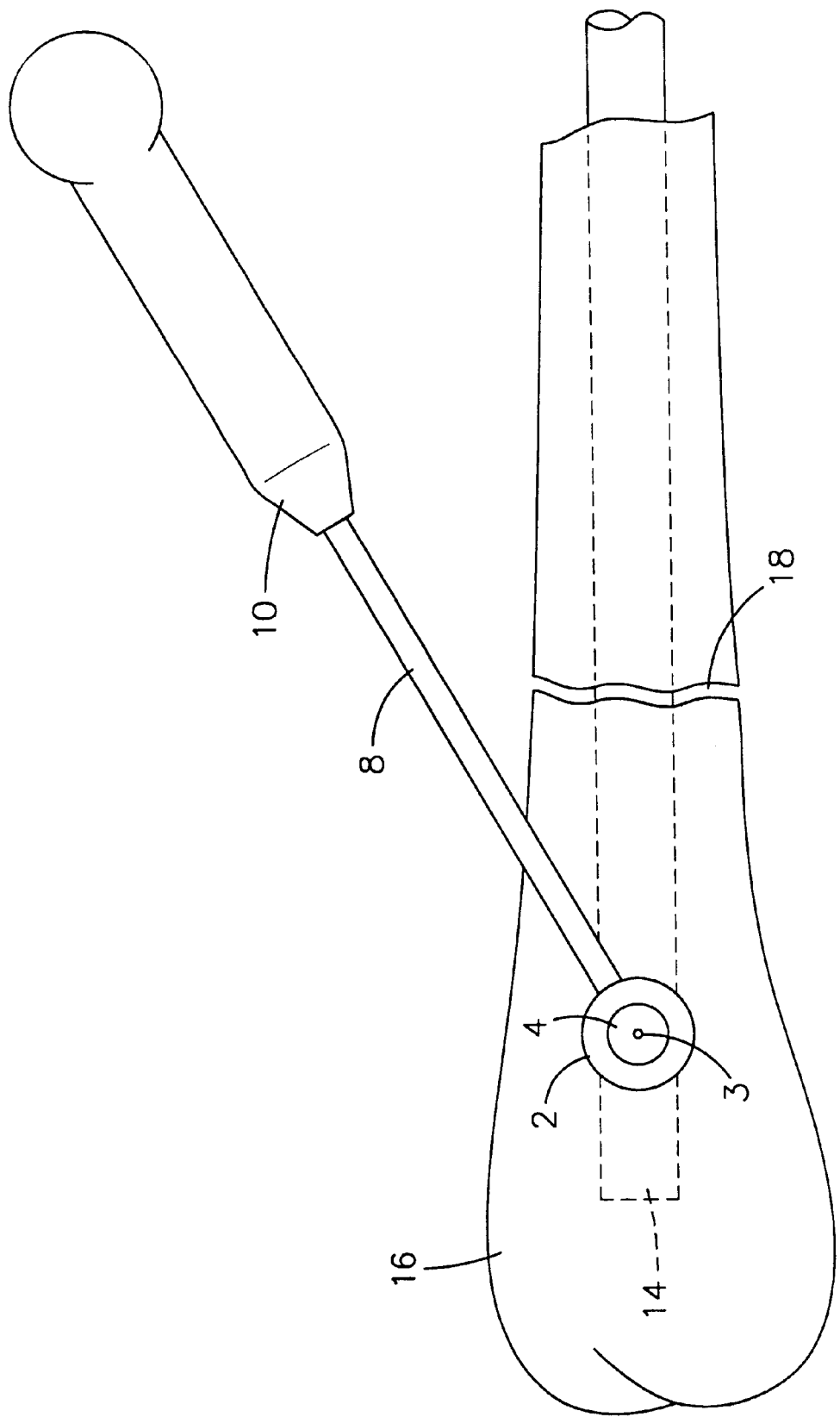
FIG. 2 is a top view of the FIG. 1 embodiment showing the relationship between a fractured bone having an osteosynthesis aid therein and a preferred embodiment in accordance with the present invention as visually represented by an X-ray imaging screen.

Referring to FIGS. 1 and 2 of the drawing, a guide sleeve with a pin and plug assembly in accordance with one embodiment of the invention is illustrated and designated generally by the numeral 100. FIG. 1 depicts the relationship between a pin and plug assembly 4 located within cannula or guide sleeve 2 having shaft 8 ending in handle 10. Pin 6 is used to visually align guide sleeve 2 coaxially with transverse hole 12 in intramedullary rod 14, using X-ray means 20, 22, and 24. It should be noted that the shaft and handle shown in FIGS. 1 and 2 are shown as an example only. An elongated handle can be employed, and it can be fixed to or removably engaged with the guide sleeve. Completely different apparatus may be used and the means for handling the guide sleeve is not considered part of the invention but only a necessary adjunct for handling the inventive elements and performing the inventive method.

Viewed from a X-ray imaging screen, the relationship between the invention and a fractured bone would be similar to FIG. 2. Intramedullary rod 14 traverses bone fracture 18 and contains holes 12 that are transverse, or perpendicular, to the longitudinal axis of the rod. Rod 14 is employed to align the bone pieces in a proper relationship to each other so that the mating edges of fracture 18 can be secured together to reunify the bone. Guide sleeve 2 is manipulated by the handle, or gripping means 10, which is connected to the guide sleeve by shaft 8. The pin and plug assembly 4 is inserted in sleeve 2 and pin 6 is maneuvered by sleeve 2 until the pin appears as a centered point over transverse rod hole 12. This indicates proper coaxial alignment between guide sleeve 2 and the rod hole.

Structure

Referring to FIGS. 3–11, description is made of the components of one embodiment of alignment apparatus 100 embodying the invention. Pin and plug assembly 4 shown in FIG. 3 comprises radiographic pin 6 encased in plug 5 made from a radiolucent material such as Lucite, or other appropriate substantially rigid radiolucent material. Thus, when viewed through a X-ray imaging screen, as shown in FIG. 2, plug 5 is translucent, but radiographic end 3 of the pin appears distinctly as a dot. Plug 5 is generally cylindrical, having a long axis with a V-shaped end 28, and a generally flat surface 30 at the opposite end. Alternatively, the pin tip 34 may extend a short distance from the plug, permitting easier penetration into the bone. In this alternative configuration, the plug 5 may have two tapered, or contoured steps, each step increasing the plug's diameter. In a preferred embodiment, the radiographic pin 6 is centrally aligned on the long axis of radiolucent plug 5. Outer surface 32 of the plug is generally smooth, for slidable engagement within guide sleeve 2.

Figure 3:
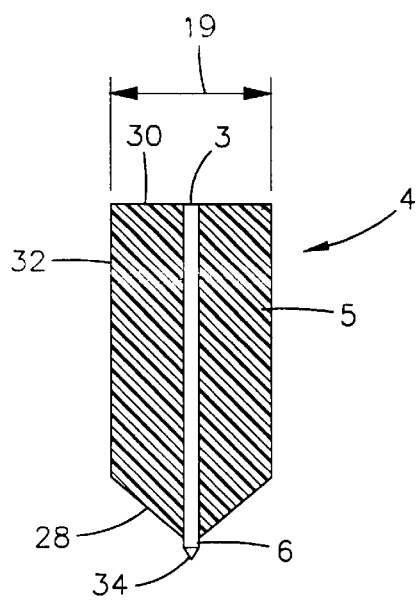
FIG. 3 is a cross-sectional view of the pin and plug assembly of FIG. 1.
Figure 4:
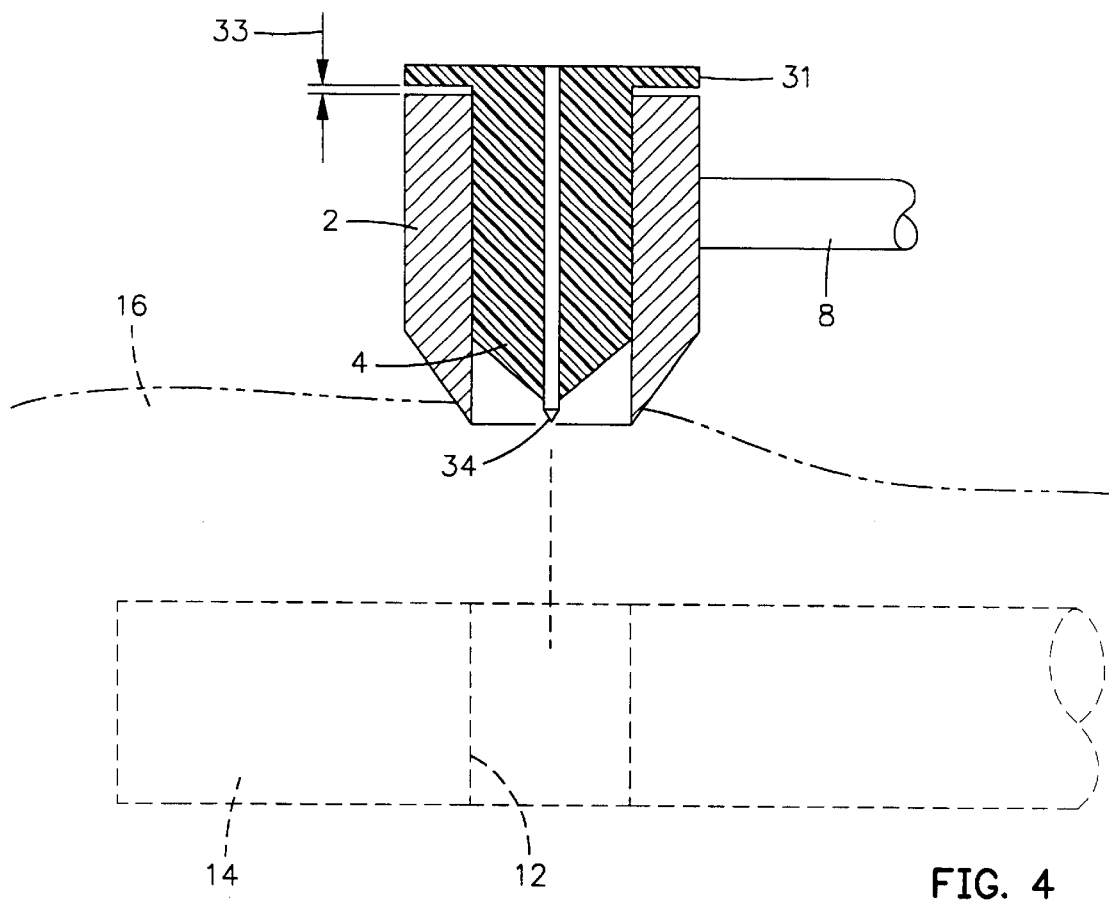
FIG. 4 is a cross-sectional view of the pin and plug assembly and a guide sleeve positioned over an osteosynthesis aid, in accordance with FIG. 1.

The radiographic pin is preferably made of a metal, such as stainless steel, or an alloy such as aluminum or titanium. End 3 of pin 6 is approximately flush with top surface 30 of the plug and the other end protrudes slightly from V-shaped end 28 of the plug, forming tip 34, as seen in FIG. 3. Alternatively, upper surface 30 may include shoulder 31, as seen in FIG. 4. Shoulder 31 extends annularly around upper surface 30, and engages upper surface 11 of guide sleeve 2, suspending the pin and plug assembly in the guide sleeve. In this alternative embodiment, the relative lengths between pin and plug assembly 4 and guide sleeve 2 may vary, forming a small gap 33 between upper surface 11 of the sleeve and the shoulder 31, when placed on the surface of bone 16, or when the sleeve is indented into the bone.

Figure 5:
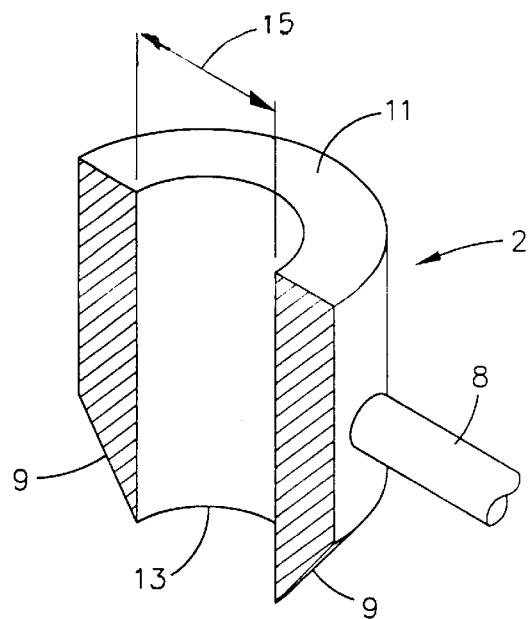
FIG. 5 is a perspective cross-sectional view of the guide sleeve of FIG. 1.

FIG. 5 depicts guide sleeve 2 separately from the assembly. Generally flat surface 11 is shown at the top, the opposite end having taper 9 culminating in sharp-edged perimeter 13. Sleeve 2 is preferably made of stainless steel, an alloy such as aluminum or titanium, carbon fiber, or another suitable material. Alternatively, only the bone-engaging surface of the sleeve is made of metal, with the rest made of a radiolucent material. The inner surface of the sleeve is generally smooth. From FIGS. 1 and 2 it can be seen that shaft 8 can be attached to the sleeve. Inner diameter 15 of the sleeve generally approximates outer diameter 19 of plug 5, with sufficient differential to permit slidable engagement of these two elements. Also, the lengths of pin and plug assembly 4 and guide sleeve 2 are relatively matched.

Figure 6:
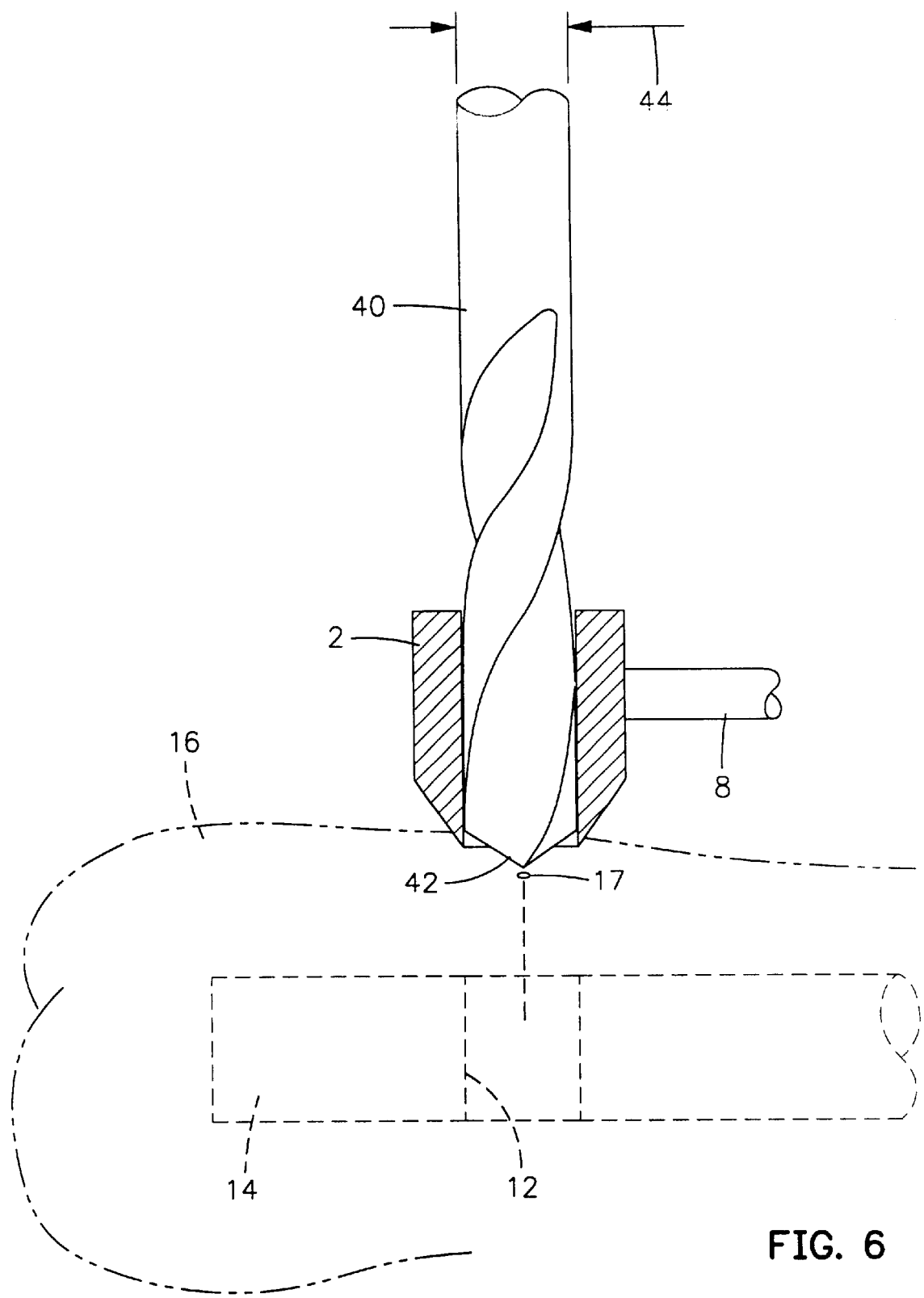
FIG. 6 shows a cross-sectional view of a guide sleeve with a drill located therein positioned over a bone indentation, in accordance with a preferred embodiment of the present invention.

The guide sleeve is also designed to accommodate solid drill 40, as shown in FIG. 6. Once the coaxial alignment operation using pin and plug assembly 4 is complete, as described later, assembly 4 is removed and a drill having tip 42 and outer diameter 44 is inserted into guide sleeve 2.

Figure 7:
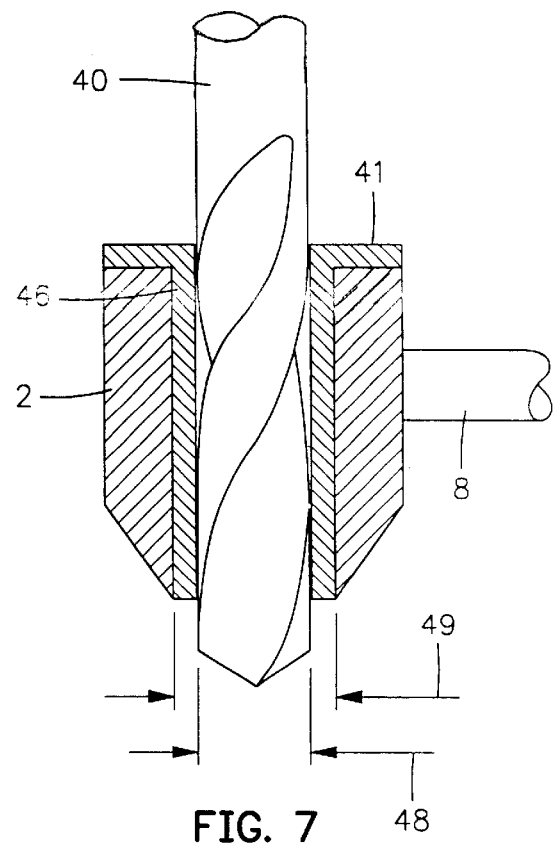
FIG. 7 is a cross-sectional view of a guide sleeve, a drill casing, and a drill in accordance with a preferred embodiment of the present invention.

In situations where diameter 44 of the drill does not generally match inner diameter 15 of the sleeve, drill casing 46 may be inserted into the sleeve, as shown in FIG. 7. Drill casing 46 can be formed of any suitable material, such as plastic, metal, or an alloy such as aluminum. Inner diameter 48 of the drill casing nearly matches external drill diameter 44 and drill casing outer diameter 49 nearly matches guide sleeve inner diameter 15, respectively, allowing slidable engagement between all three elements.

Drill casing 46 may be formed with annular shoulder 41 that engages sleeve upper surface 11, suspending the casing in the guide sleeve. Additionally, the drill casing may have a key, or a plurality of keys 50, shown in FIG. 9, on shoulder 41 engaging mating keyways 52 on upper surface 11 of the sleeve.

Figure 8:
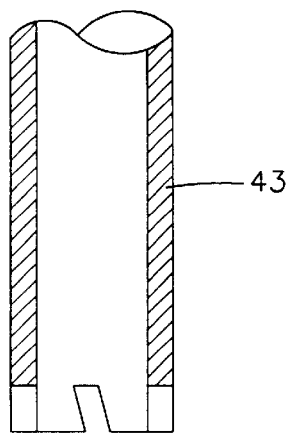
FIG. 8 is a cross-sectional view of a guide sleeve, a guide wire casing, and a guide wire for use with a hollow drill in accordance with an alternative embodiment of the invention.
Figure 9:
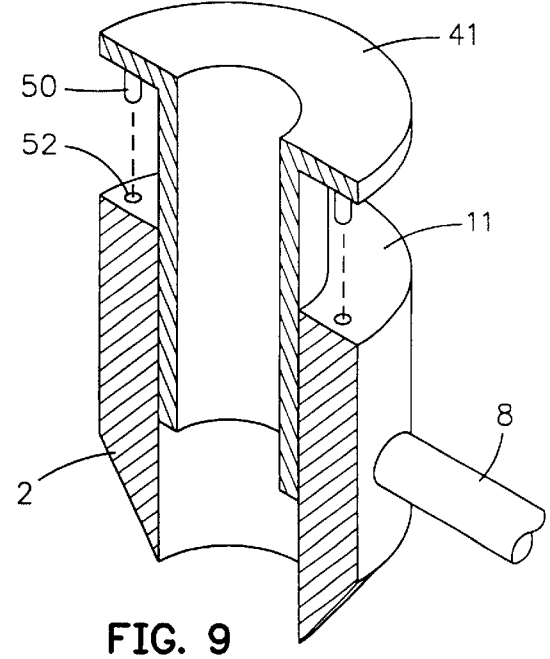
FIG. 9 is a perspective cross-sectional view showing a guide sleeve and a casing for a drill, guide wire, or fastener, with mating keys and keyway, in accordance with another alternative embodiment of the invention.

Alternatively, a guide wire 51, as shown in FIG. 8, can be used to guide a hollow drill 43. Guide wire casing 53, having the same slideable engagement features and circumferential shoulder as drill casing 46, would be inserted in guide sleeve 2. The guide wire can be composed of a metal such as stainless steel, or an alloy such as aluminum or titanium. The guide wire casing can be composed of any suitable material including an alloy such as aluminum, or a plastic. The guide wire can be employed to form the indentation in the bone and can be drilled into the bone. Sleeve 2 can be removed because a hollow drill would be guided on guide wire 51 during the drilling procedure.

Figure 10:
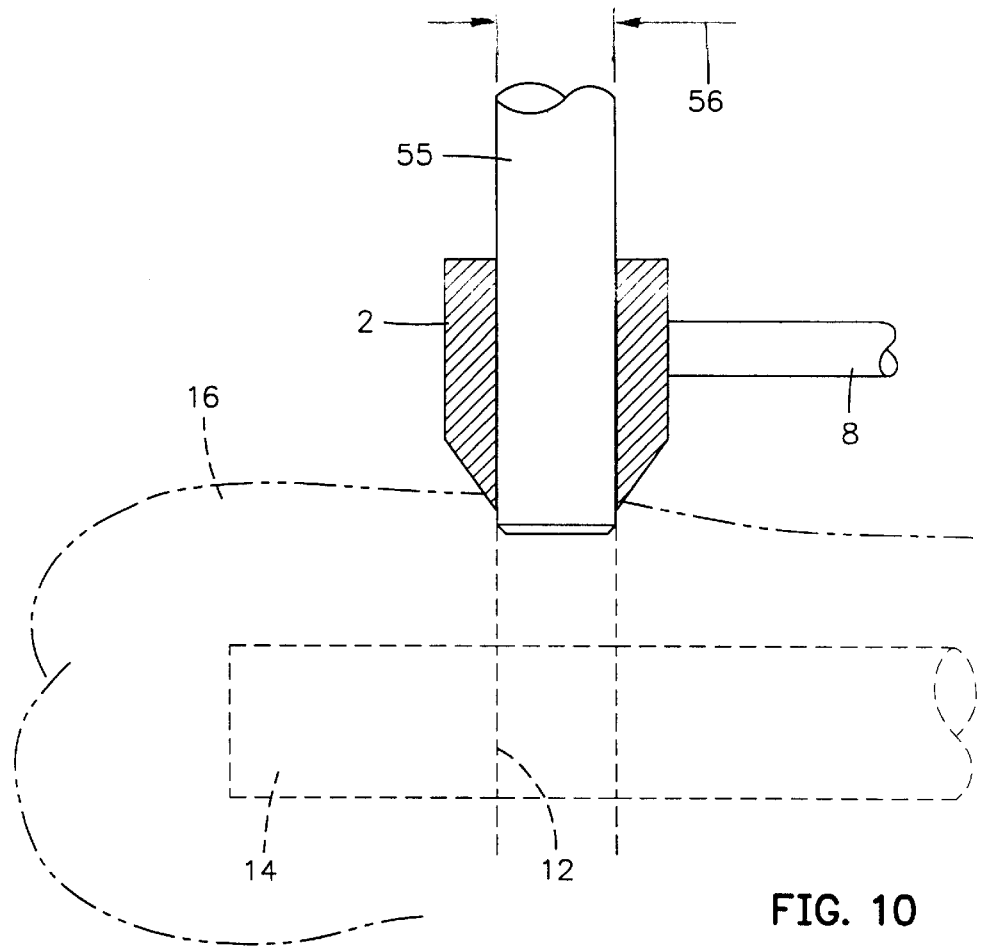
FIG. 10 is a cross-sectional view of a guide sleeve and a fastener located over a hole drilled in a bone in accordance with a preferred embodiment of the invention.

As a further aspect of the invention, guide sleeve 2 is also designed to accommodate fastener 55, as shown in FIG. 10. The fastener can be a screw, pin, or other joining device, made from a suitable material such as metal, alloy, or plastic. Once the drilling operation is complete, as described later, the fastener, having outer diameter 56, is placed in the guide sleeve 2.

Figure 11:
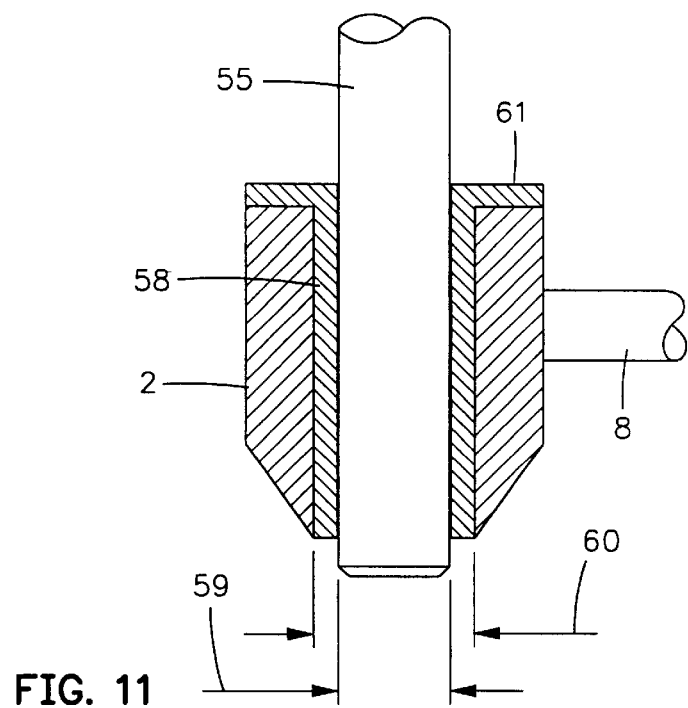
FIG. 11 is a cross-sectional view of a guide sleeve, fastener casing, and a fastener located therein in accordance with another embodiment of the invention.

In situations where the fastener diameter does not generally match the inner diameter of the sleeve, fastener casing 58 may be inserted into the sleeve, as shown in FIG. 11. The fastener casing can be composed of any suitable material, such as either plastic, metal, or an alloy such as aluminum or titanium. Inner diameter 59 of the fastener casing nearly matches fastener diameter 56, and outer diameter 60 of the fastener casing nearly matches the inner diameter of the guide sleeve, respectively, allowing slidable engagement between all three elements. The fastener casing may be formed with annular shoulder 61 that engages sleeve upper surface 11, suspending the casing in the guide sleeve. Additionally, the fastener casing may have a key or a plurality of keys on shoulder 61, engaging equivalent keyways on upper surface 11, in the manner shown in FIG. 9.

Operation

Figure 12:
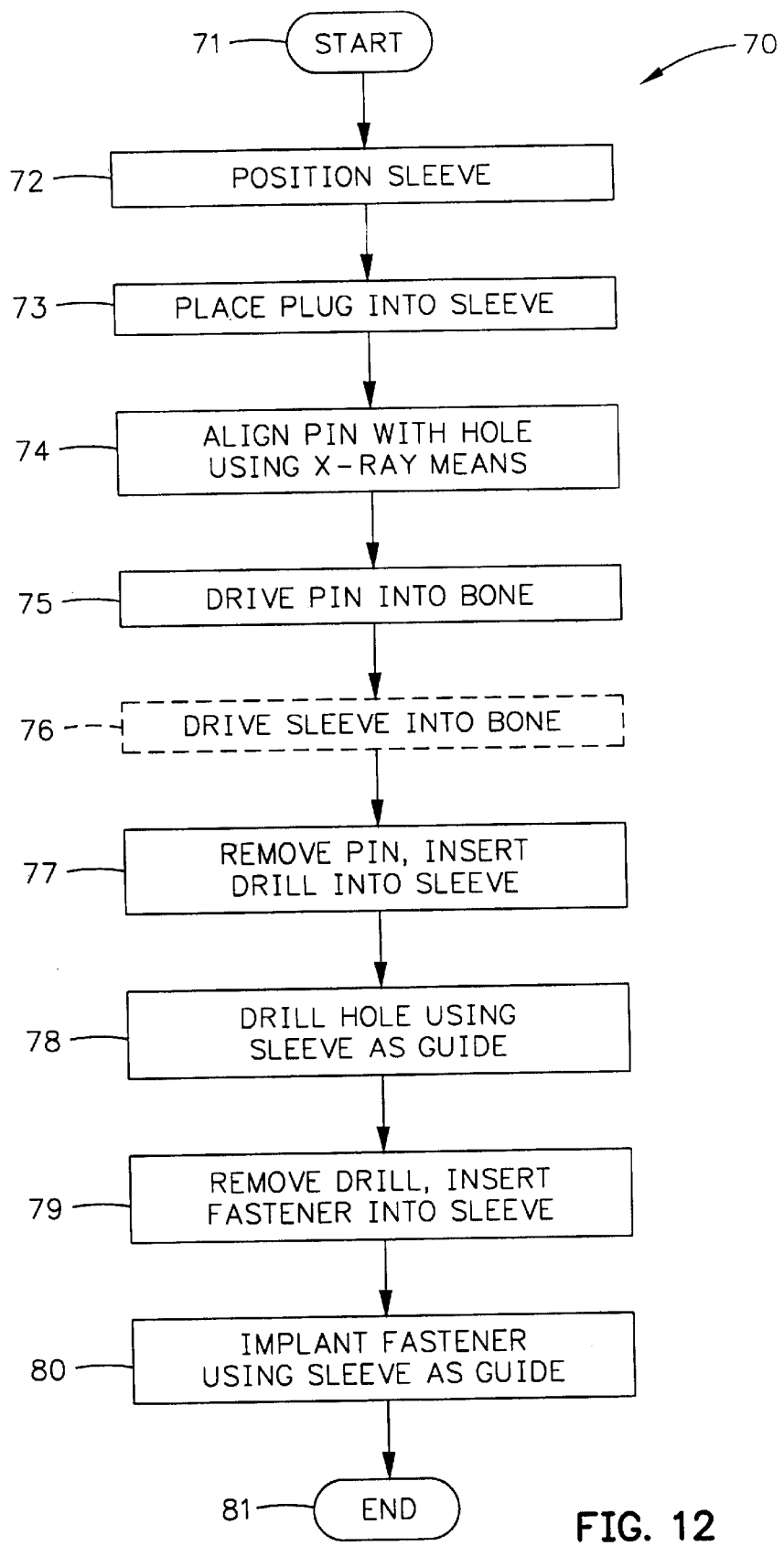
FIG. 12 is a flowchart illustrating an exemplary sequence of method steps in accordance with the invention.

Broadly, the method of the invention concerns aiming and coaxially aligning an apparatus for hole forming in a patient's bone, drilling a hole in the bone and rotationally fixing the bone with respect to an intramedullary rod inserted in the bone. FIG. 12 depicts a specific example of the method of the present invention, in the form of a sequence of tasks 70, which is described primarily with respect to FIGS. 1 and 2.

The procedure starts at 71. In task 72, guide sleeve 2 is placed close to a patient's damaged bone into which intramedullary rod 14, having one or more transverse holes, has been placed. In task 73, pin and plug assembly 4 is placed in guide sleeve 2, with the V-shaped end 28 next to the bone. In step 74, the X-ray apparatus is positioned and energized and bone 16, transverse rod hole 12, guide sleeve 2, and pin and plug assembly 4 are viewed through an X-ray imaging screen 24. Pin 6 is maneuvered over rod hole 12 until the pin is coaxially aligned therewith. The pin appears as point 3 (FIG. 2) when correct coaxial alignment is achieved.

Task 75 is completed when a striking means strikes the pin and plug assembly driving pin tip 34 into the bone creating pilot hole, or indentation 17, seen in FIG. 6. Optional step 76 is preferably performed next. Guide sleeve 2 is struck with striking means, driving sharp-edged perimeter 13 into bone 16, creating an indentation therein. This fixes the guide sleeve relative to the bone, ensuring correct coaxial alignment throughout the operation. Alternatively, pin and plug assembly 4 and guide sleeve 2 can be struck simultaneously, driving both the pin tip and sharp-edged perimeter into the bone at the same time. Alternatively, pin and plug assembly 4 and guide sleeve 2 can be pressed against the bone.

Tasks 77 and 78 are depicted in FIG. 6. Drill 40 is inserted into guide sleeve 2 after pin and plug assembly 4 has been removed. Drill tip 42 rests in the indentation 17 made by pin tip 34. The indentation starts drill 40 at the correct point, and guide sleeve 2 guides the drill along the correct axis during the drilling operation. FIG. 7 shows drill casing 46, which may be used when drill diameter 44 is smaller than guide sleeve inner diameter. The drill casing is placed in the guide sleeve before the drill, and ensures correct coaxial alignment of the drill and the guide sleeve.

Alternatively, guide wire 51 and guide wire casing 53 can be placed into the guide sleeve after the pin and plug assembly has been removed. The guide wire is drilled, or driven into the bone, then guide wire casing 53 is removed, and a hollow drill is placed in the guide sleeve 2, around guide wire 51.

FIG. 11 depicts tasks 79 and 80. Fastener 55 is inserted into guide sleeve 2 after the drill has been removed. The fastener can be a screw, pin, or other joining device, made from a suitable material such as metal, alloy, or plastic. The guide sleeve guides fastener 55 along the correct axis as it engages the bone and the hole in the implanted intramedullary rod.

Other Embodiments

While there has been shown what are presently considered to be preferred embodiments of the invention, it will be apparent to those skilled in the art that various modifications and improvements can be made herein without departing from the scope of the invention as defined by the appended claims.

An alternate embodiment of the invention may be constructed with a sleeve of a non-circular dimension that may fit a particular bone surface. This would require a non-circular pin and plug assembly. Drill casings, and guide wire casings, with substantially different inner and outer diameters are also possible. Alternative materials may be used for the different components including the sleeve, pin, plug, drill casing, guide wire casing, fastener casing and handle assembly. The drill and fastener casings may comprise only one device, instead of two, or means other than a keyway may be used to fix either casing to the guide sleeve.

What is claimed is:

1. An apparatus for determining and maintaining coaxial alignment with a transverse hole in an osteosynthesis aid in a patient's bone, using X-ray means, comprising:
   a cannula having two ends, wherein one end is shaped and configured to form an indentation in the bone to establish and maintain the desired position of the cannula relative to the bone; and
   a pin and plug assembly comprising a radiographic pin encased in a radiolucent plug, the assembly being removably mounted in the cannula, wherein the pin appears as a centered point when proper alignment is determined.

2. The apparatus of claim 1, wherein the two ends of the cannula are circular and one circular end is tapered to form a sharp-edged perimeter.

3. The apparatus of claim 1, and further comprising application means for handling or holding the cannula in place.

4. The apparatus of claim 1, wherein the pin and plug assembly is slidably engaged in the cannula.

5. The apparatus of claim 1, wherein the cannula is composed of a material selected from the group consisting of stainless steel, aluminum, titanium and carbon fiber.

6. The apparatus of claim 1, wherein the radiolucent plug containing the radiographic pin has two ends, with one end being V-shaped.

7. The apparatus of claim 6, wherein the radiographic pin has a sharp end located at the tip of the V-shaped plug, and a relatively flat end located at the other end of the plug.

8. The apparatus of claim 1, wherein the radiolucent plug is composed of a relatively rigid radiolucent material.

9. The apparatus of claim 1, wherein the radiographic pin is composed of a material selected from the group consisting of stainless steel, aluminum, and titanium.

10. The apparatus of claim 1, and further comprising a drill casing shaped and configured to be slidably inserted into the cannula.

11. The apparatus of claim 1, and further comprising a fastener casing shaped and configured to be slidably inserted into the cannula.

12. The apparatus of claim 1, and further comprising a guide wire casing shaped and configured to be slidably inserted into the cannula.

* * * * *